US011219726B2

(12) United States Patent
Tatkov et al.

(10) Patent No.: US 11,219,726 B2
(45) Date of Patent: Jan. 11, 2022

(54) RESPIRATORY ASSISTANCE DEVICE AND A METHOD OF CONTROLLING SAID DEVICE

(71) Applicant: Fisher & Paykel Healthcare Limited, Auckland (NZ)

(72) Inventors: Stanislav Tatkov, Auckland (NZ); Kevin Peter O'Donnell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 76 days.

(21) Appl. No.: 16/415,607

(22) Filed: May 17, 2019

(65) Prior Publication Data

US 2019/0336712 A1 Nov. 7, 2019

Related U.S. Application Data

(63) Continuation of application No. 14/776,994, filed as application No. PCT/NZ2014/000041 on Mar. 14, 2014, now Pat. No. 10,342,942.
(Continued)

(51) Int. Cl.
*A61M 16/00* (2006.01)
*A61M 16/06* (2006.01)
(Continued)

(52) U.S. Cl.
CPC ...... *A61M 16/0069* (2014.02); *A61M 15/009* (2013.01); *A61M 16/0003* (2014.02);
(Continued)

(58) Field of Classification Search
CPC ............ A61M 16/0069; A61M 15/009; A61M 16/0003; A61M 16/024; A61M 16/0666; A61M 16/0875; A61M 16/104; A61M 16/12; A61M 16/122; A61M 16/16; A61M 16/1015; A61M 2016/003; A61M 2016/0027; A61M 2016/0039; A61M 2202/0208; A61M 2202/0225; A61M 2202/0241; A61M 2205/3334
See application file for complete search history.

(56) References Cited

U.S. PATENT DOCUMENTS 4,686,974 A 8/1987 Sato et al.
5,148,802 A 9/1992 Sanders et al.
(Continued)

FOREIGN PATENT DOCUMENTS

WO WO 2008/058328 5/2008
WO WO 2013/163685 11/2013

OTHER PUBLICATIONS

International Search Report; PCT/NZ2014/000041; dated Jun. 13, 2014; 7 pages.

*Primary Examiner* — Steven O Douglas
(74) *Attorney, Agent, or Firm* — Knobbe, Martens, Olson and Bear, LLP

(57) ABSTRACT

A method of controlling a flow rate of gases supplied to a patient by a respiratory assistance device includes controlling the supply gases flow rate so as to deliver gases to the patient according to a predetermined gases pressure/flow rate profile for at least a portion of the breathing cycle. A profile may be achieved that provides the patient with a particular benefit or therapy.

22 Claims, 6 Drawing Sheets

Related U.S. Application Data

(60) Provisional application No. 61/788,849, filed on Mar. 15, 2013, provisional application No. 61/944,800, filed on Feb. 26, 2014.

(51) Int. Cl.
  *A61M 16/12* (2006.01)
  *A61M 16/16* (2006.01)
  *A61M 15/00* (2006.01)
  *A61M 16/08* (2006.01)
  *A61M 16/10* (2006.01)

(52) U.S. Cl.
  CPC ...... *A61M 16/024* (2017.08); *A61M 16/0666* (2013.01); *A61M 16/0875* (2013.01); *A61M 16/104* (2013.01); *A61M 16/12* (2013.01); *A61M 16/122* (2014.02); *A61M 16/16* (2013.01); *A61M 16/1015* (2014.02); *A61M 2016/003* (2013.01); *A61M 2016/0027* (2013.01); *A61M 2016/0039* (2013.01); *A61M 2202/0208* (2013.01); *A61M 2202/0225* (2013.01); *A61M 2202/0241* (2013.01); *A61M 2205/3334* (2013.01)

(56) References Cited

U.S. PATENT DOCUMENTS

| | | |
|---|---|---|
| 5,165,397 A | 11/1992 | Arp |
| 6,152,129 A * | 11/2000 | Berthon-Jones ............ A61M 16/0057 128/200.24 |
| 6,467,477 B1 | 10/2002 | Frank et al. |
| 6,948,497 B2 | 9/2005 | Zdrojkowski et al. |
| 7,827,981 B2 | 11/2010 | Bamford |
| 8,020,558 B2 | 9/2011 | Christopher et al. |
| 8,225,796 B2 | 7/2012 | Davenport et al. |
| 8,333,194 B2 | 12/2012 | Lewis et al. |
| 8,522,782 B2 | 9/2013 | Lewis et al. |
| 10,342,942 B2 | 7/2019 | Tatkov et al. |
| 2002/0078958 A1 | 6/2002 | Stenzler |
| 2003/0168067 A1 | 9/2003 | Dougill et al. |
| 2005/0011523 A1 | 1/2005 | Aylsworth et al. |
| 2006/0000475 A1 | 1/2006 | Matthews et al. |
| 2006/0011195 A1 | 1/2006 | Zarychta |
| 2007/0175473 A1 | 8/2007 | Lewis et al. |
| 2008/0142019 A1 | 6/2008 | Lewis et al. |
| 2009/0107501 A1 | 4/2009 | Krieger |
| 2011/0253136 A1 | 10/2011 | Sweeney et al. |
| 2013/0104888 A1 | 5/2013 | Landis et al. |
| 2013/0340752 A1 | 12/2013 | Landis et al. |
| 2014/0048070 A1 | 2/2014 | Wedler et al. |

* cited by examiner

RESPIRATORY ASSISTANCE DEVICE AND A METHOD OF CONTROLLING SAID DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to a method of controlling a respiratory assistance device and to a respiratory assistance device.

Description of the Related Art

Respiratory assistance devices are often used where a patient or other user requires assistance when breathing. This may be to assist in providing sufficient air to the patient during normal breathing or to treat a particular condition, such as sleep apnoea, for example. These may be used when in hospital, or at home, for example.

Depending on the treatment or patient needs, gases other than air may be used and/or used to supplement air. For example, air may be supplemented with oxygen to provide a patient with oxygen-enriched air. Other chemicals, compositions, or medicaments may also be added or alternatively used. Further, the gases may be humidified to provide for improved patient comfort.

Respiratory assistance devices typically comprise a respiratory gases source, such as a supply of pressurised gases and/or a gases flow generator such as a blower or compressor. The respiratory gases source delivers gases to a patient via an inspiratory conduit connected to a patient interface such as a full face mask, a nasal mask, or a nasal cannula, for example. The gases may be delivered at a pressure greater than atmospheric pressure to assist in delivering sufficient gases to the lungs of the patient and/or to provide respiratory support, for example, during treatment of chronic obstructive pulmonary disease (COPD).

During normal respiration (unassisted breathing), the pressure and flow rate within the airway of a patient vary. During inspiration, the pressure rapidly decreases from ambient pressure to a maximum negative pressure as the diaphragm moves downward. This causes air to be drawn into the airway with an increasing flow rate, initiating at near zero flow. As inspiration ends, the pressure returns toward ambient pressure and the flow rate returns to near zero. During subsequent expiration, the pressure rises as the diaphragm moves upward, generating increasing flow in the opposite direction (i.e., out of the airway). As expiration continues, the pressure tails off toward ambient pressure and the flow rate returns to near zero for commencement of the next inhalation.

Due to the physiological stress that a patient may experience in an intensive care unit (ICU), the patient can have a higher than usual demand for oxygen and often require a much greater level of ventilation compared to a normal, healthy patient. The patient can exert an increased level of effort of breathing trying to meet this demand and to ensure adequate ventilation. This increased level of effort means that the patient is expending greater metabolic effort and so producing more carbon dioxide ($CO_2$). To remove the $CO_2$ and keep respiratory gases concentrations at a safe level requires even greater ventilation, and therefore even greater effort. As the patient continually tries to increase the effort to breathe and is unable to adequately expire the increasing amounts of $CO_2$ produced, the patient can experience respiratory muscle fatigue and develop hypercapnia.

Elevated levels of $CO_2$ can also occur in a patient due to an obstructive disease such as asthma. Excess mucous in the airway and bronchoconstrictions can inhibit breathing and result in the respiratory muscles being unable to provide sufficient ventilation to meet the metabolic demands of the patient.

Respiratory assistance devices have been proposed which attempt to control their operation to better align with the changing needs of a patient during the breathing cycle.

For example, U.S. Pat. No. 5,148,802 describes an apparatus for providing alternating high and low positive pressures in the airway of a patient. The pressure levels are coordinated with the spontaneous respiration of the patient such that the disclosed apparatus provides lower positive pressure during exhalation than during inhalation, to decrease resistance experienced during exhalation. To achieve this, it is necessary for the disclosed apparatus to monitor the breathing cycle of the patient to determine when to switch between the pressure levels. Flow is monitored to determine instantaneous and average flow rates, with inhalation detected if the instantaneous flow rate is greater than the average flow rate and exhalation detected if the instantaneous flow rate is less than the average flow rate, and with the pressure levels being adjusted accordingly. While the disclosed apparatus may provide for some improved comfort for a patient, the instant inventors have recognised that the control provided thereby is not ideal. For example, during inhalation, when there is less resistance to the gases being delivered to the lungs since there is no opposing air flow as there is during exhalation, there may be no need to increase pressure.

The inventors have further recognised that flow resistance in the airway of a patient is proportional to the flow restriction in the nasal cavities of the patient. Indeed around 50% of the resistance to flow is provided by the nasal cavities. This nasal resistance is present during normal respiration and when the patient is provided with respiratory assistance. For example, during continuous positive airway pressure (CPAP) treatment, gases are delivered to a patient at an elevated pressure, but the resistance to flow remains the same. Consequently, the profile of pressure against gases flow rate during CPAP is the same as the profile during normal, unassisted respiration, but with the profile shifted on the pressure axis by the amount of pressure elevation. Prior art devices have at least not fully accounted for this relatively significant nasal resistance to flow, with flow being monitored based on measurements taken along the delivery path to, but prior to reaching, the patient.

It can be desirable to use a nasal high flow or jet delivery system, rather than a face mask based arrangement for some therapies. Further, some patients may prefer such interfaces based on perceived comfort levels. At present, such devices generally deliver gases at a fixed flow rate.

OBJECT OF THE INVENTION

It is an object of the invention to provide a method of controlling a respiratory assistance device and/or a respiratory assistance device which overcomes or at least ameliorates one or more of the disadvantages of the prior art.

Alternatively, it is an object to at least provide the public or industry with a useful choice.

Further objects of the invention will become apparent from the following description.

SUMMARY OF THE INVENTION

In a first aspect, the invention may broadly be said to consist in a method of controlling a flow rate of respiratory gases supplied to a patient by a respiratory assistance device arranged to be in fluid communication with an inspiratory conduit and a patient interface to deliver gases to the patient, and comprising or arranged to be in fluid communication with a respiratory gases source, the method comprising:

controlling the flow rate of respiratory gases supplied to the patient according to a predetermined gases pressure/flow rate profile in a mode defined for at least a portion of a breathing cycle of the patient, wherein the predetermined gases pressure/flow rate profile is configured to alter the flow rate at the end of expiration and/or the beginning of inspiration to increase the clearance of anatomical dead space in the patient.

Preferably, the controlling comprises:

controlling the flow rate of respiratory gases supplied to the patient according to a first predetermined gases pressure/flow rate profile in a first mode, and controlling the flow rate of respiratory gases supplied to the patient according to a second predetermined gases pressure/flow rate profile in a second mode, wherein the second predetermined gases pressure/flow rate profile is different to the first predetermined gases pressure/flow rate profile.

Preferably the method comprises an additional step of controlling the flow rate of respiratory gases supplied to the patient according to at least one further predetermined gases pressure/flow rate profile in at least one further mode.

Preferably the flow rate of respiratory gases supplied to the patient is controlled according to the further profile between inspiration and expiration.

Preferably the further profile is configured such that the flow rate of respiratory gases is supplied to the patient at a pressure determined by a pressure set point.

Preferably the set point corresponds to the positive end expiratory pressure (PEEP).

Preferably the or each profile is configured to achieve at least one of a plurality of predetermined physiological effects or benefits to the patient.

For example, the or each profile may be configured to achieve at least one of:

an increase in inspiratory pressure to reduce inspiratory resistance;

an increase or decrease in expiratory resistance;

an increase in the flow rate of respiratory gases supplied to the patient at the end of expiration and/or beginning of inspiration to increase clearance of anatomical dead space independently of inspiratory and/or expiratory pressure; or an increase in the flow rate of respiratory gases supplied to the patient to meet peak inspiratory demand independently of generated pressure during inspiration and/or expiration to accurately deliver oxygen or other respiratory or anaesthetic gases, aerosols, humidity, etc.

Preferably, during one or more of the modes, the flow rate of respiratory gases supplied to the patient is controlled such that the respiratory gases are supplied at a substantially constant pressure for at least a predetermined portion of the breathing cycle.

Preferably, during one or more of the modes, the flow rate of respiratory gases supplied to the patient is controlled such that the respiratory gases are supplied at varying pressures for at least a predetermined portion of the breathing cycle.

Preferably the or each profile is configured to provide a supply of gas tailored to the patient's respiratory needs at one or more points in the breathing cycle.

Preferably at least one profile is determined in dependence upon providing a desired pressure characteristic to the patient.

Preferably at least one profile is determined on the basis of the pressure in the airway of the patient.

Preferably at least one profile is configured such that the pressure of the respiratory gases supplied to the patient always equals or exceeds the pressure required by the patient.

Preferably at least one profile is determined in dependence upon providing a desired therapeutic effect to the patient.

Preferably the flow rate of respiratory gases supplied to the patient is controlled according to more than one of the profiles during inspiration and/or expiration.

Preferably the first profile corresponds to an inspiration mode and/or the second profile corresponds to an expiration mode.

Preferably the first profile is determined independently of the second profile.

Preferably the flow rate of respiratory gases supplied to the patient is controlled to supply respiratory gases in pulses at a relatively high flow rate.

Preferably the flow rate of respiratory gases supplied to the patient is controlled to supply respiratory gases continuously at a relatively high flow rate.

Preferably the flow rate of respiratory gases supplied to the patient is between about 10 and 80 L/min.

Alternatively, the flow rate of respiratory gases supplied to the patient may be between about 1 and 20 L/min. The lower flow rate may be more appropriate for a child, for example.

Preferably the flow rate of respiratory gases supplied to the patient is controlled in dependence upon a resistance to gases flow provided by the nasal cavities of the patient.

Preferably the controlling comprises dynamically controlling the flow rate of respiratory gases supplied to the patient over time.

Preferably the controlling comprises varying the flow rate of respiratory gases supplied to the patient.

Preferably the controlling comprises varying the flow rate of respiratory gases supplied to the patient and the varying is performed when switching between the modes and/or during one or more of the modes.

Preferably the controlling comprises varying at least one of:

an impedance of a gases flow path between the respiratory gases source and a patient interface; and a flow rate of respiratory gases in the gases flow path.

Preferably varying the impedance of the gases flow path is achieved through use of a valve or flow restrictor.

Alternatively, or additionally, varying the flow rate of respiratory gases is achieved by controlling the speed of a motor of a gases flow generator that comprises, or is arranged to be in fluid communication with, the respiratory gases source.

Alternatively, or additionally, the respiratory gases source may comprise a source of pressurised gas. For example, the respiratory gases source may comprise or be connected to a cylinder of gases and/or gases provided via a compressor.

Such gases may provide all or only a portion of the gases supplied to a patient. For example, such a supply may be used to supplement air provided to a patient. For example, air may be driven toward a patient and enriched along its path with oxygen.

Preferably pressure is determined by calculation from at least one of:
  a pressure measured by a pressure sensor;
  a flow rate measured by a flow sensor;
  a motor speed; and
  a known pressure drop across the gases flow path/circuit.

The pressure may be determined via a pressure sensor which may be located, for example, in a pressure line that is separate from the patient interface. The pressure sensor may be positioned (and/or pressure may be measured) anywhere between the nasal cavity and the respiratory gases source. The pressure may be determined by calculation from, for example, at least one of: motor speed, known pressure drop across the gases flow path/circuit, and flow rate measured from a flow sensor. Known processes can be used to determine pressure drops associated with particular items of equipment.

Preferably the supply gases flow rate is controlled in dependence upon the resistance to gases flow provided by the nasal cavities of the patient.

In a second aspect, the invention may broadly be said to consist in a method of controlling the flow rate of respiratory gases supplied to a patient by a respiratory assistance device arranged to be in fluid communication with an inspiratory conduit and a patient interface to deliver gases to the patient, and comprising or arranged to be in fluid communication with a respiratory gases source, the method comprising:
  controlling the flow rate of respiratory gases supplied to the patient according to a predetermined gases pressure/flow rate profile in a mode defined for at least a portion of a breathing cycle of the patient, wherein the predetermined gases pressure/flow rate profile is configured to control the flow rate of respiratory gases supplied to the patient such that respiratory gases are supplied at a substantially constant pressure for a predetermined portion of the breathing cycle.

Preferably said controlling comprises:
  controlling the flow rate of respiratory gases supplied to the patient according to a first predetermined gases pressure/flow rate profile in a first mode; and
  controlling the flow rate of respiratory gases supplied to the patient according to a second predetermined gases pressure/flow rate profile in a second mode,
  wherein the second predetermined gases pressure/flow rate profile is different to the first predetermined gases pressure/flow rate profile.

Preferably the first profile is configured to control the flow rate of respiratory gases supplied to the patient such that respiratory gases are supplied at a first substantially constant pressure for a predetermined portion of the inspiratory phase of the breathing cycle;
  the second profile is configured to control the flow rate of respiratory gases supplied to the patient such that respiratory gases are supplied at a second substantially constant pressure for a predetermined portion of the expiratory phase of the breathing cycle; and
  the first substantially constant pressure is different to the second substantially constant pressure.

Preferably the controlling comprises dynamically controlling the flow rate of respiratory gases supplied to the patient over time.

Preferably the controlling comprises varying the flow rate of respiratory gases supplied to the patient.

Preferably the controlling comprises varying the flow rate of respiratory gases supplied to the patient and the varying is performed when switching between the modes and/or during one or more of the modes.

Preferably the controlling comprises varying at least one of:
  an impedance of a gases flow path between the respiratory gases source and a patient interface; and
  a flow rate of respiratory gases in the gases flow path.

Preferably varying the impedance of the gases flow path is achieved through use of a valve or flow restrictor.

Preferably varying the flow rate of respiratory gases is achieved by controlling the speed of a motor of a gases flow generator that comprises, or is arranged to be in fluid communication with, the respiratory gases source.

Preferably the respiratory gases source comprises a source of pressurised gas.

Preferably pressure is determined by calculation from at least one of:
  a pressure measured by a pressure sensor;
  a flow rate measured by a flow sensor;
  a motor speed; and
  a known pressure drop across the gases flow path/circuit.

In a third aspect, the invention may broadly be said to consist in a respiratory assistance device arranged to be in fluid communication with an inspiratory conduit and a patient interface to deliver gases to a patient, and comprising or arranged to be in fluid communication with a respiratory gases source, the respiratory assistance device comprising:
  a controller operative to control a flow rate of respiratory gases supplied to the patient according to a predetermined gases pressure/flow rate profile in a mode defined for at least a portion of a breathing cycle of the patient,
  wherein the predetermined gases pressure/flow rate profile is configured to achieve a predetermined physiological effect or benefit to the patient.

Preferably the respiratory assistance device is operative according to at least one or more of:
  a first mode in which the controller varies the flow rate of respiratory gases supplied to the patient according to a first predetermined gases pressure/flow rate profile; and
  a second mode in which the controller varies the flow rate of respiratory gases supplied to the patient according to a second predetermined gases pressure/flow rate profile; and
  wherein the second predetermined gases pressure/flow rate profile is different to the first predetermined gases pressure/flow rate profile.

Preferably at least one of the profiles is configured to increase the flow rate at the end of expiration and/or the beginning of inspiration to increase clearance of anatomical dead space in the patient.

Preferably at least one of the profiles is configured to control the flow rate of respiratory gases supplied to the patient such that respiratory gases are supplied at a substantially constant pressure for a predetermined portion of the breathing cycle.

Other features of the respiratory assistance device of the third aspect are analogous to the steps recited in relation to the methods of the first and second aspects.

In a fourth aspect, the invention may broadly be said to consist in a method of adjusting a respiratory assistance device arranged to be in fluid communication with an inspiratory conduit and a patient interface to deliver gases to a patient, and comprising or arranged to be in fluid communication with a respiratory gases source, the method comprising:

measuring one or more of the positive end expiratory pressure, inspiratory pressure, or expiratory pressure of the patient, the gases pressure in a gases flow path between the respiratory gases source and the patient airway during inspiration, or the gases pressure in the gases flow path during expiration; and determining, and/or adjusting, a first predetermined gases pressure/flow rate profile and/or a second predetermined gases pressure/flow rate profile for controlling the flow rate of respiratory gases supplied to the patient in dependence upon the or at least one said measured pressure.

The supply gases flow rate may therefore be controlled and/or adjusted in dependence upon the measurements made to achieve the desired gases pressure/flow rate profile.

Preferably the flow rate of respiratory gases supplied to the patient is controlled and/or adjusted in dependence upon the measurements made to achieve the or each profile.

Preferably the method further comprises acquiring an identification of a type of conduit and/or patient interface. Different profiles may be required dependent on the equipment used for a particular application (e.g., different types of conduits or patient interfaces can affect flow and/or pressure differently, for example, in terms of resistance to flow).

Preferably the identification is acquired via a user input or via an identification tag associated with the equipment or via an electrical resistance associated with the equipment.

Preferably the identification may include data indicative of at least one of: patient name, date, gas flow rate, or gas pressure.

Preferably the method further comprises a step to measure PEEP and/or IP and/or EP and/or inspiration gas pressure and/or expiration gas pressure at different gas flow rates.

Preferably the method further comprises a step of providing an indication of a property or characteristic of the device or the measurements.

Preferably the method further comprises a step of adjusting the flow rate of respiratory gases supplied to the patient by adjusting the motor speed of a fan motor comprising, or arranged to be in fluid communication with, the respiratory gases source. The motor may be an electronically commutated (EC) motor arranged to receive a direct current (DC) supply current, to invert the DC supply to an alternating current (AC) output, and to control motor speed via control of the inverter. Such a motor has variable speed, and is able to change motor speed relatively quickly.

In a fifth aspect, the invention may broadly be said to consist in a method of controlling the flow rate of gas supplied to a patient by a respiratory assistance device, the method comprising controlling the supply gas flow rate so as to deliver gas to the patient according to a predetermined gas pressure-flow rate profile for at least a portion of the breathing cycle.

The method of the fourth aspect may be used in association with the respiratory assistance device of the third aspect of the invention, or as a precursor to, or during, administration of patient therapy according to the method of the first, second, or fifth aspects of the invention.

Further aspects of the invention, which should be considered in all its novel aspects, will become apparent from the following description.

BRIEF DESCRIPTION OF THE DRAWINGS

A number of embodiments of the invention will now be described by way of example with reference to the drawings in which.

DETAILED DESCRIPTION OF THE PREFERRED EMBODIMENT

Figure 1:
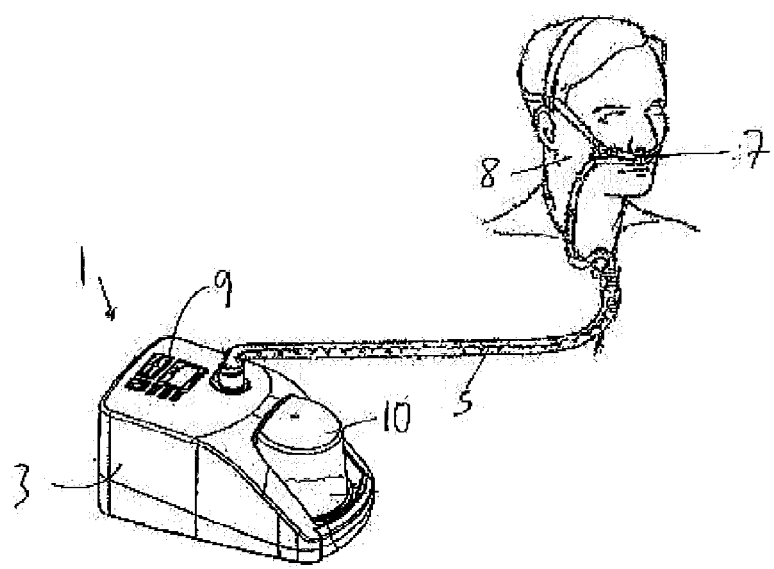
FIG. 1 is an overview of a respiratory assistance device in accordance with the invention.
Figure 2:
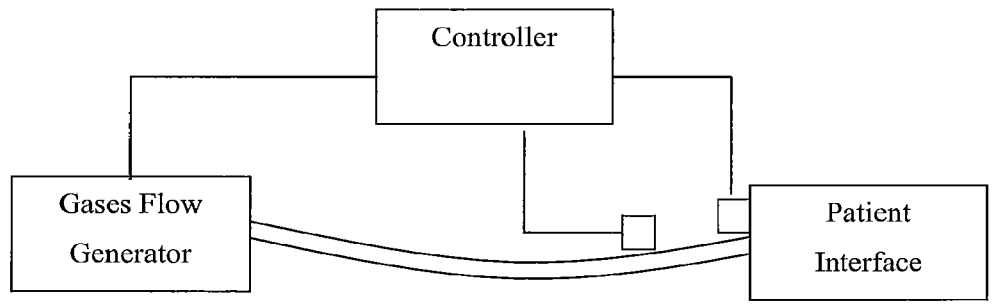
FIG. 2 is a schematic of a first respiratory assistance device in accordance with the invention.
Figure 3:
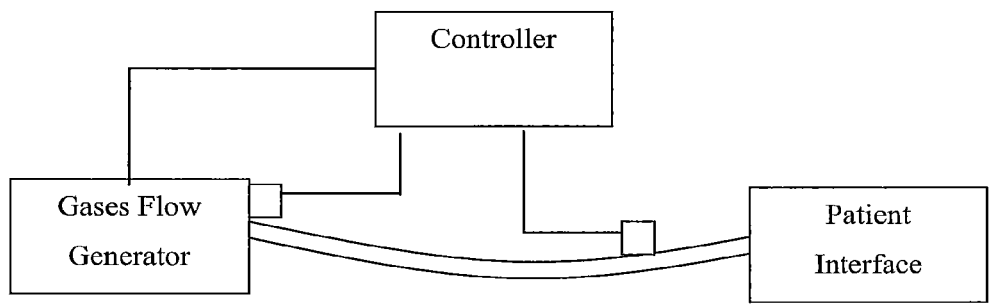
FIG. 3 is a schematic of a second respiratory assistance device in accordance with the invention.

Throughout the description, like reference numerals will be used to refer to like features in different embodiments.

Referring to the figures, an embodiment of a respiratory assistance device 1 comprises a respiratory gases source 3 and is arranged to be in fluid communication with an inspiratory conduit 5 and a patient interface 7 to deliver respiratory gases to a patient 8. In an alternate embodiment (not shown), the respiratory gases source 3 is separate from, and arranged to be in fluid communication with, the respiratory assistance device 1. The respiratory assistance device 1 further comprises a controller 9 that is operative to control the respiratory assistance device 1. In some embodiments, the respiratory assistance device 1 further comprises a humidifier 10 to heat and humidify the respiratory gases delivered to the patient 8.

The respiratory gases source 3 may incorporate, or be connected to, a blower comprising a motor driving a fan to supply respiratory gases to the patient 8. The inspiratory conduit 5 may comprise any suitable type of tubing or the like to form a gases flow path between the respiratory gases source 3 and the patient 8 via the patient interface 7.

The patient interface 7 in this example comprises a nasal cannula. One form of nasal cannula typically comprises tubing that extends around the ears to the nose of the patient, with an inlet/outlet duct or prong being provided at or in each nare and in fluid communication with the tubing. Another form of nasal cannula typically comprises similar inlet/outlet ducts or prongs in fluid communication with tubing held in position by headgear, such as one or more headstraps. In some cases the tubing may be provided with an exhaust duct or vent. It will be appreciated that any other form of patient interface may alternatively be used, including a full or partial face mask for example and/or a hybrid thereof.

The controller 9 may comprise an electronic controller, which may be microprocessor-based, for example. The controller 9 is operative to control the respiratory assistance device 1 according to a first mode in which the supply gases flow rate from the respiratory gases source 3 is controlled according to a first predetermined pressure/flow rate profile; and preferably to further control the respiratory assistance device 1 according to a second mode in which the supply gases flow rate from the respiratory gases source 3 is controlled according to a second predetermined pressure/ flow rate profile; the second pressure/flow rate profile being different to the first pressure/flow rate profile.

The resulting gases flow rate in the gases flow path may be dynamically varied and/or adjusted to achieve a desired pressure/flow rate profile, that is, to achieve a desired gases flow rate and a desired pressure in the gases flow path over a period of time, and preferably over the duration of the breathing cycle. By achieving such a profile, the delivery of gases to the patient 8 can be controlled in such a way as to provide certain benefits, advantages or therapies to the patient 8, and/or to avoid or ameliorate certain disadvantages or problems. The control can also be such that the profile is achieved for all, or only certain portions of the inspiratory and expiratory phases of the breathing cycle. Different profiles can be achieved for the inspiratory and expiratory phases of the breathing cycle.

In one example, the respiratory gases source 3 comprises a high speed motor, such as an electronically commutated (EC) or direct current (DC) brushless motor which drives a fan of a blower and is controlled by the controller 9. A flow sensor 13 is provided in the gases delivery path between the respiratory gases source 3 and the patient 8. The controller 9 comprises a memory, or is connected to an external memory, on which a relationship between motor speed and gases pressure within the gases flow path, is stored. This relationship may have been determined via laboratory testing or in situ testing of the respiratory assistance device 1, as explained further below.

The controller 9 then controls the respiratory assistance device 1, and thus the respiratory gases source 3, according to a first mode in which a first predetermined gases pressure/flow rate profile is achieved. The first profile may be based on a target inspiratory gases flow rate predetermined either via a suitable algorithm provided on the controller 9, or via an operator input. The controller 9 controls the motor speed to achieve the target gases flow rate, on the basis of the predetermined relationship between motor speed and gases pressure. The controller 9 is operative to continuously monitor and control the motor speed to achieve the first gases pressure/flow rate profile. In other embodiments, the gases flow rate may be controlled by the use of a controllable valve or flow restrictor, either alone or in combination with a variable-speed blower motor.

The gases pressure/flow rate profile may be based on a constant value gases flow rate, for example, through the inspiratory phase of the breathing cycle. After the peak in inspiration, the gases flow rate will start to fall and so the controller 9 will reduce the motor speed in relatively small increments until the gases flow rate starts to increase again, immediately after the peak in expiration. At this point, the controller 9 may again increase the motor speed such that the gases flow rate at least equals or exceeds the requirements of the patient 8.

In another example, a pressure sensor 15 is provided at or inside the patient interface 7 to measure the pressure in the airway of the patient 8, or at least to measure the pressure in the gases flow path as close to the airway as possible. The controller 9 receives a signal from the pressure sensor 15 and processes this to control the motor speed to achieve a predetermined pressure level. For example, it may be desirable to maintain a constant pressure level for all or part of the inspiratory and/or expiratory phases of the breathing cycle, or to achieve different pressure levels during inspiration and expiration.

In another example, the pressure drop across the gases flow path may be measured and input to the controller 9. In this circumstance, the pressure sensor 15 may be mounted on the high pressure side of the respiratory gases source 3, the relationship between pressure drop and gases flow rate along the gases flow path being stored on or referenced by the controller such as via a lookup table or database. The controller 9 then controls the motor speed, and hence the supply gases flow rate, with reference to the known pressure drop and additional pressure measurements made by the pressure sensor 15, to achieve a predetermined pressure/flow rate profile. This profile may be configured such that the pressure at the patient interface 7 is at a known flat level.

In a further example, the controller 9 is arranged to measure and store the pressure change within the gases flow path with upper airway and tidal volume, over a number of breathing cycles for a fixed motor speed. This is done at, or as close to, the desired target flow rate as possible. The controller 9 can subsequently control the motor speed such that the pressure change is near zero for example.

It is envisaged that the respiratory assistance device 1 could be used with a patient interface 7 comprising a semi-sealed cannula. A semi-sealed cannula may be arranged to permit exhaust of the gases flow when a predetermined pressure is exceeded, for example during expiratory flow when the flow from the respiratory assistance device 1 is combined with the flow from the lungs of the patient 8. Such a cannula is typically arranged not to allow exhaust of gases flow below a predetermined pressure, for example during inspiration. This would serve to exaggerate the flow difference between inspiration and expiration which could subsequently be controlled by varying the motor speed during the inspiratory and expiratory phases of the breathing cycle using any of the methods described above.

Variable nasal high flow (VNHF) can be achieved by controlling the motor speed to vary the flow rate. Alternatively VNHF can be achieved by varying the impedance within the flow path of the system, for example via application of variable (relatively low) back pressure.

Figure 4A:
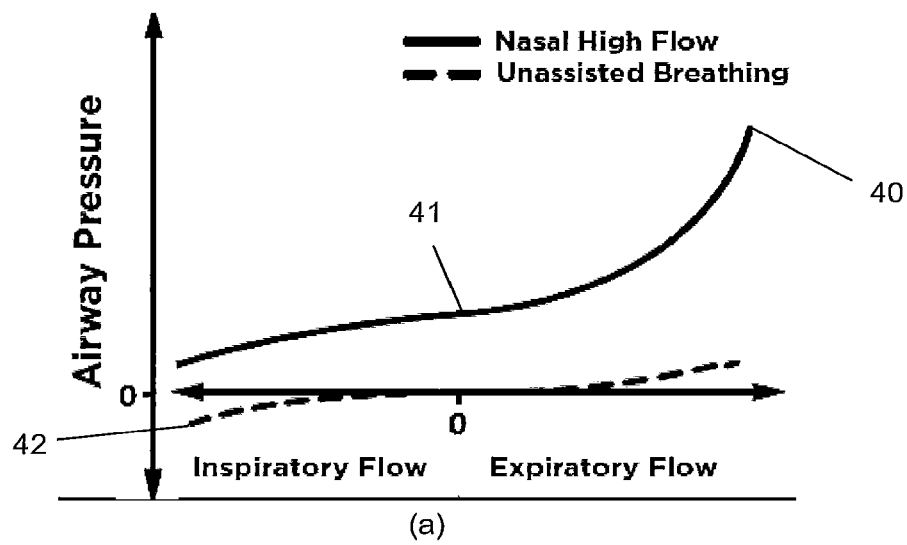
FIGS. 4A and 4B are graphs relating airway pressure to patient flow and time, respectively, for unassisted breathing and an example variable nasal high flow (VNHF) method and respiratory assistance device in accordance with the invention.
Figure 4B:
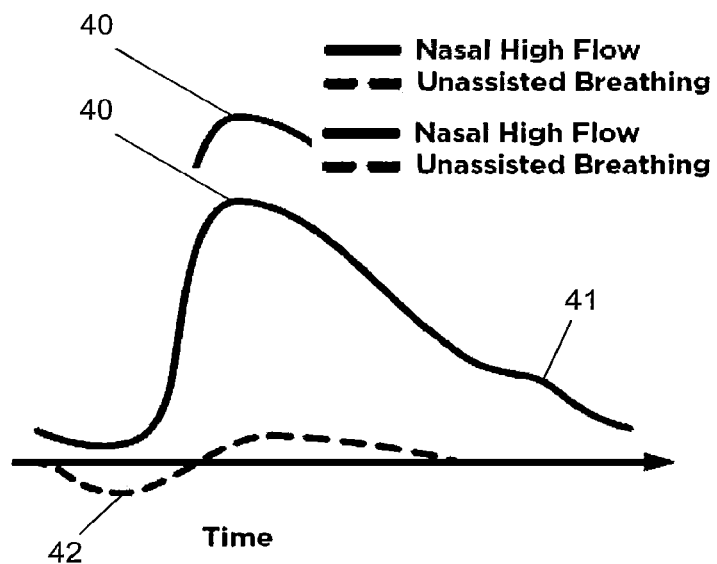

Referring to FIGS. 4A and 4B, the relationships between airway pressure and patient flow rate (FIG. 4A) and time (FIG. 4B) are shown for both normal respiration (unassisted breathing) and respiration during VNHF therapy. The respective pressure/flow rate profiles are substantially as shown in FIG. 4A. In this example, the VNHF supply gases flow rate from the source of pressurized gases is controlled to remain substantially constant, for example at 15 litres per minute (L/min) throughout inspiration and expiration such that the gases pressure increases gradually from peak inspiration to peak expiration. This provides pressure relief during expiration. FIG. 4B shows a single complete breathing cycle (i.e., including an expiratory phase and an inspiratory phase). In both of the figures the peak expiratory pressure 40, positive end expiratory pressure (PEEP) 41, and peak inspiratory pressure 42 can be observed.

Figure 5A:
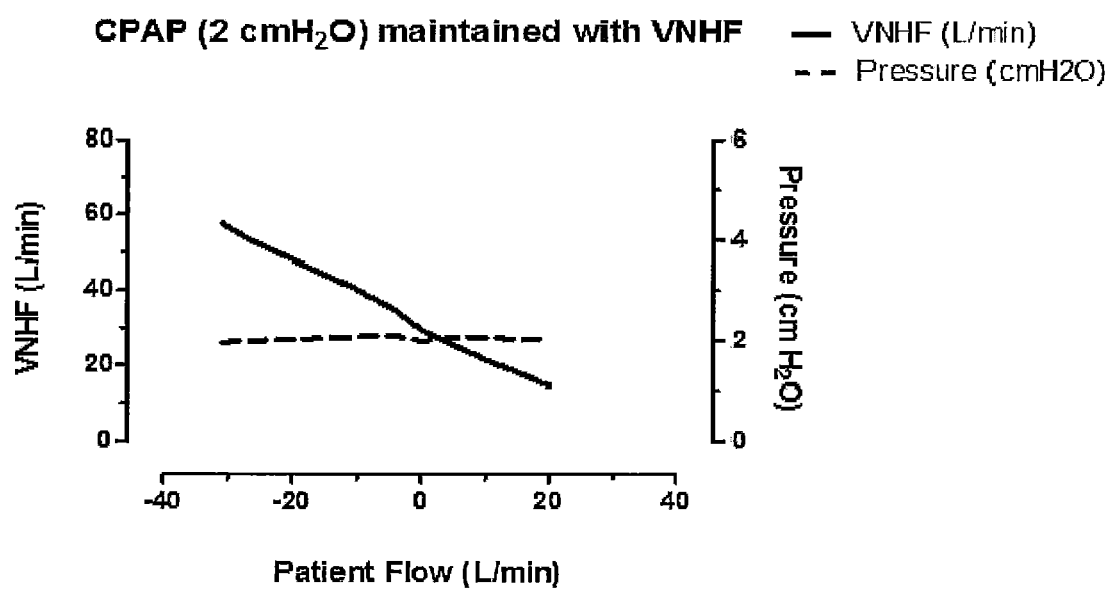
FIGS. 5A-5C are graphs showing further example gases pressure/flow rate profiles used with a method and a respiratory assistance device in accordance with the invention.

Referring to FIG. 5A, in a further example, the supply gases flow rate from the respiratory gases source 3 is controlled to decrease between peak inspiration and peak expiration such that the gases pressure remains substantially constant at a medium value of about 2 centimetres of water ($cmH_2O$). VNHF is different from non-invasive ventilation (NV, for example using a full face mask), where inspiratory pressure (IP) is higher than expiratory pressure (EP). With VNHF, it would be highly unlikely to achieve a high IP. In this example, positive airway pressure is maintained at 2 $cmH_2O$ throughout the duration of the respiratory cycle with VNHF.

Figure 5B:
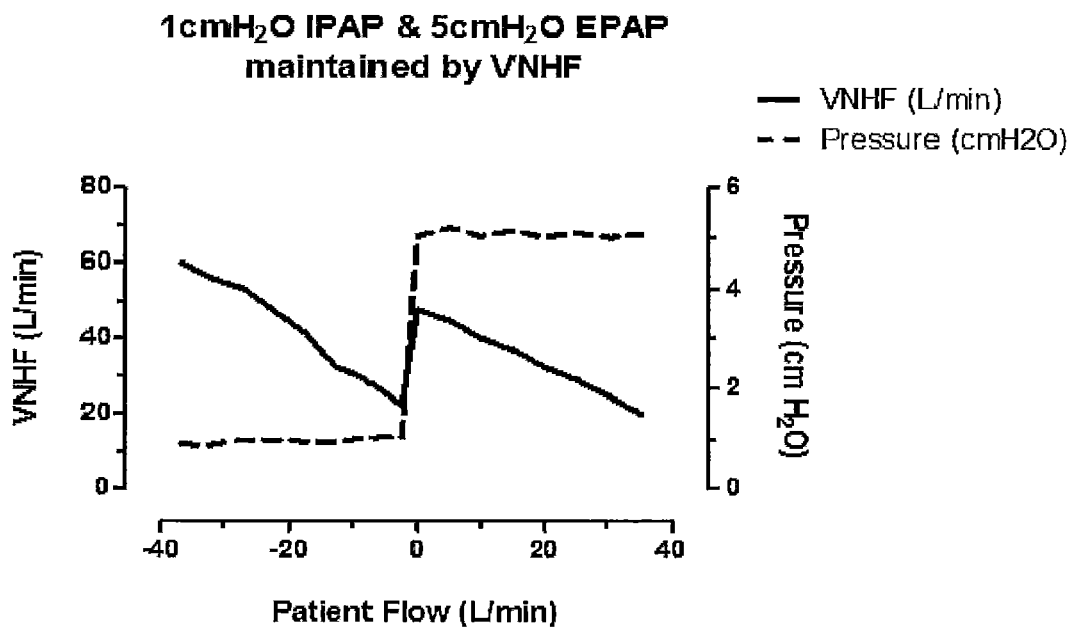

Referring to FIG. 5B, another example gases pressure/flow rate profile is shown for the inspiratory and expiratory phases of the breathing cycle. Thus the respiratory assistance device 1 is operative according to a first profile during inspiration (where the patient flow is shown as negative), and a second profile during expiration (where the patient flow is shown as positive). In this example, the gases flow rate from the respiratory gases source 3 is controlled such that the gases pressure during inspiration is substantially constant and relatively low, held at about 1 cmH$_2$O. Thus the supply gases flow rate from the respiratory gases source 3 is controlled to reduce during inspiration. Between inspiration and expiration, the supply gases flow rate from the respiratory gases source 3 is controlled to rise substantially vertically, such that the gases pressure also rises substantially vertically, with the patient gases flow substantially zero. During expiration, the supply gases flow rate from the respiratory gases source 3 is controlled such that the pressure remains substantially constant and relatively high, held at about 5 cmH$_2$O. Thus the supply gases flow rate from the respiratory gases source 3 is again controlled to reduce during expiration. A decrease of the supply gases flow rate during expiration can keep expiratory pressure steady or prevent a high increase. It can be particularly useful in a hybrid mask where leakage (biased flow) is not high, and flow during inspiration should be higher than during expiration. Here positive airway pressure is maintained at alternating values of 1 cmH$_2$O and 5 cmH$_2$O throughout the duration of the respiratory cycle with VNHF.

Figure 5C:
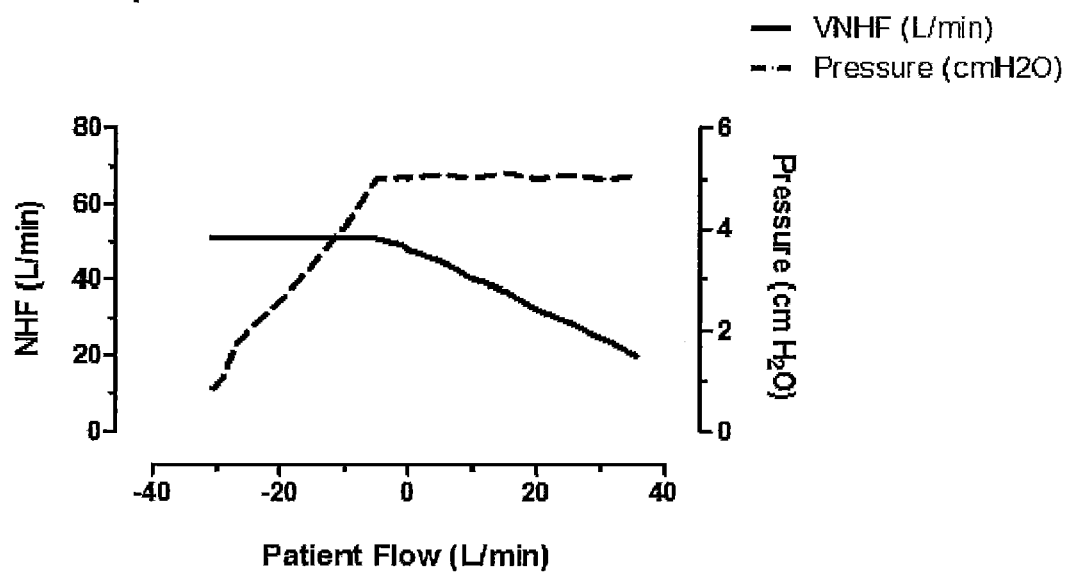

Referring to FIG. 5C, in another example, the supply gases flow rate from the respiratory gases source 3 is controlled to remain substantially constant during inspiration such that the gases pressure rises gradually from 1 cmH$_2$O toward a relatively high peak of around 5 cmH$_2$O. Slightly before expiration, when the inspiratory gases flow rate from the patient 8 is approaching zero, the supply gases flow rate from the respiratory gases source 3 is controlled to decrease such that the gases pressure during expiration remains substantially constant and relatively high, at about 5 cmH$_2$O.

The patient 8 may experience physiological stress in an intensive care unit (ICU) that makes it more difficult to breathe because the patient 8 is unable to adequately expire the increasing amounts of $CO_2$ produced in the airway of the patient 8. The patient 8 may also have an obstructive disease, such as asthma, that can inhibit breathing. In either case, the patient 8 may benefit greatly from the clearance of anatomical dead space, also referred to as $CO_2$ flushing, as a way to help regulate $CO_2$ levels.

In one approach, $CO_2$ may be removed from the airway of the patient 8 during the expiratory pause, immediately before the beginning of inspiration. At this point, the gases in the airway make up the initial volume of the following breath, so flushing the airways at this point reduces rebreathed $CO_2$. However, high flow rates during expiration can result in uncomfortable pressure and noise. In particular, flushing the $CO_2$ at the end of expiration may cause incomplete expiration. In another approach, therefore, $CO_2$ may be removed from the airway of the patient 8 at the beginning of inspiration, or at the end of expiration and the beginning of inspiration.

Figure 6A:
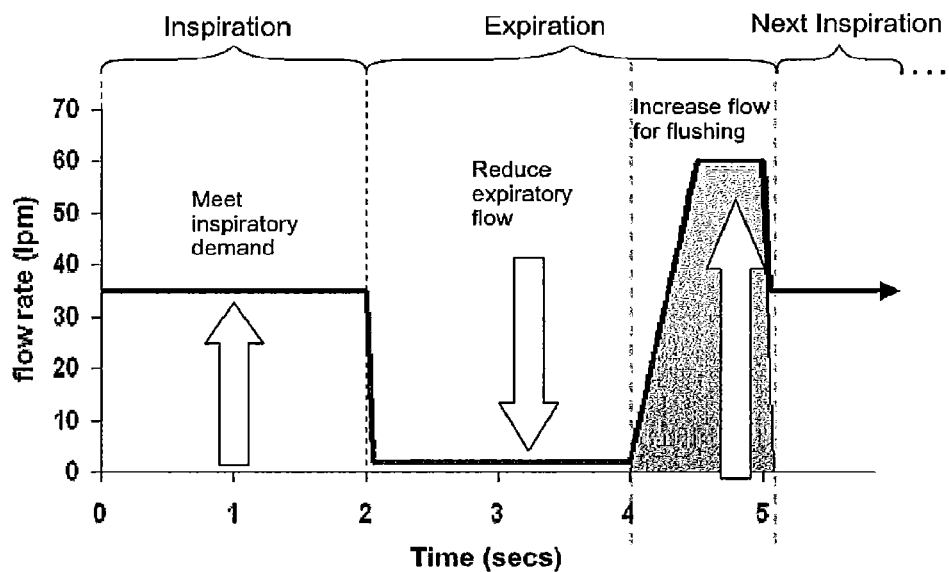
FIGS. 6A and 6B demonstrate varying the flow rate and pressure for the clearance of anatomical dead space according to embodiments of a method and a respiratory assistance device of the present invention.
Figure 6B:
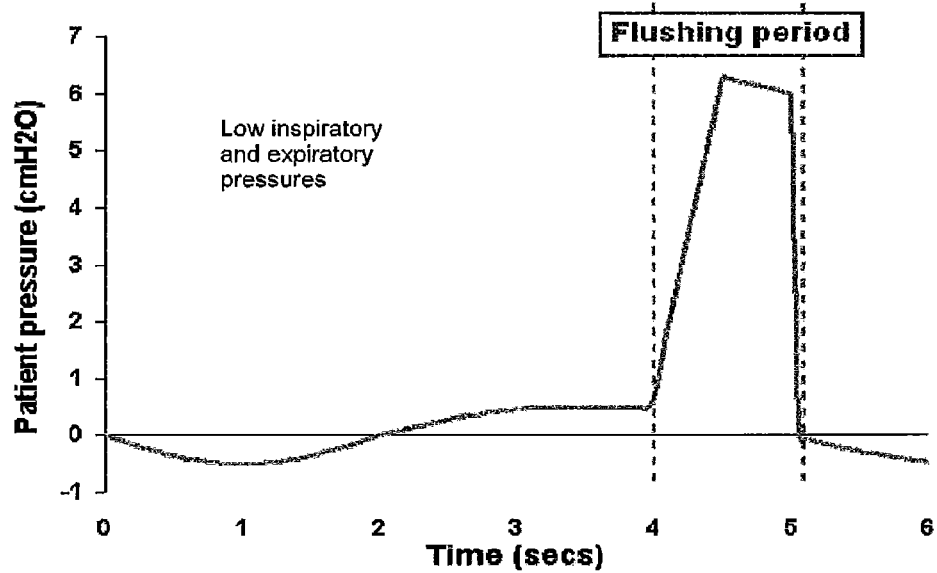

Referring to FIGS. 6A and 6B, an example variation of the flow rate and pressure to increase clearance of dead space is shown. The respiratory assistance device 1 is operative according to a first profile during inspiration to deliver the illustrated constant inspiratory flow rate that meets the peak inspiratory demand of the patient 8, a second profile during expiration to avoid unnecessary additional flow and therefore pressure, and a further profile during a "flushing period" substantially between expiration and inspiration. In this example, the first profile delivers a flow rate of approximately 35 L/min and the second profile delivers a flow rate of approximately 2 L/min. In other embodiments, the flushing period may alternatively form part of the first or second profiles.

The supply gases flow rate from the respiratory gases source 3 is controlled to rapidly decrease at the start of expiration to about 2 L/min to aid expiratory effort and reduce the potentially uncomfortable sharp increase in pressure and noise that can be felt by the patient 8 at this point. In the flushing period, about 1 second before the start of inspiration, the supply gases flow rate from the respiratory gases source 3 is controlled to increase, reaching for example about 60 L/min after about 0.5 seconds, and then to be held at about 60 L/min for the last about 0.5 seconds of expiration. At the start of the next inspiration, the supply gases flow rate from the respiratory gases source 3 is controlled to drop back to about 35 L/min.

This method of varying the flow rate targets flushing at the expiratory pause while reducing or minimising the effect of a rapid pressure increase felt by the patient 8 at the start of expiration. The timing of the flushing and the duration of the flushing period may be determined by measuring and taking the average length of expiration over a number of the previous breathing cycles, and may also be customised to the patient 8 in some embodiments. In some embodiments, the flow rate may be increased in the flushing period to levels lower than 60 L/min, but is typically increased to at least 25 L/min for adults.

The changes in flow rate within or between each profile may be substantially instantaneous, or there may be a ramp up to and/or ramp down from the peak flow rate. These ramps may have the same or unequal gradients. There may also be multiple flushing phases within a flushing period. For example, there may be a ramp up to one flow rate level that is held for a period of time and then the flow rate may change to a second level for a second period of time. The flushing period may follow various waveform shapes. In the illustrated example, the flow rate is increased to a predetermined level and then held for a period of time. In alternative embodiments, the flow rate during flushing may resemble a triangular or sinusoidal wave, for example.

Any other desired gases pressure/flow rate profile can be achieved as required to provide the desired benefit, treatment or therapy to the patient 8. Any number of profiles can be used, within the breathing cycle or within any part of it.

The respiratory assistance device 1 may be used initially in a test or calibration mode in which pressure measurements are made under controlled conditions by measuring one or more of the PEEP, IP, or EP of the patient 8, the gases pressure in a gases flow path between the respiratory gases source 3 and the airway of the patient 8 during inspiration, or the gases pressure in the gases flow path during expiration. At least one of these measurements may be used to subsequently determine, and/or adjust, the first pressure/flow rate profile in dependence upon at least one said measured pressure. The controller 9, when in the testing or calibration mode, may refer to a look-up table or database of pressure and/or flow rate characteristics of the inspiratory conduit 5 and/or patient interface 7 to be used with the respiratory assistance device 1. For example, a cannula may have different pressure and/or flow rate characteristics from a full face mask, and the controller 9 may refer to these characteristics to control the respiratory device 1 to achieve the desired pressure/flow rate profile accordingly.

The supply gases flow rate may therefore be controlled and/or adjusted in dependence upon the measurements made to achieve the desired gases pressure/flow rate profile. Particular pressure measurements may be associated with further particular modes of operation and/or the particular equipment forming the inspiratory conduit 5 and/or the patient interface 7.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. A method of controlling a flow rate of respiratory gases supplied to a patient, the method comprising:
   controlling the flow rate of respiratory gases supplied to the patient according to a predetermined gases flow rate profile in a mode defined for at least a portion of a breathing cycle of the patient,
   wherein the predetermined gases flow rate profile is configured to control the flow rate of respiratory gases supplied to the patient such that respiratory gases are supplied at a substantially constant pressure over the entire expiratory phase of the breathing cycle wherein the flow rate is variable, and
   wherein the respiratory gases are supplied to the patient using a nasal cannula.

2. The method of claim 1, wherein controlling the flow rate of respiratory gases comprises:
   controlling the flow rate of respiratory gases supplied to the patient according to a first predetermined gases pressure/flow rate profile in a first mode; and
   controlling the flow rate of respiratory gases supplied to the patient according to a second predetermined gases pressure/flow rate profile in a second mode,
   wherein the second predetermined gases pressure/flow rate profile is different to the first predetermined gases pressure/flow rate profile.

3. The method of claim 2, wherein:
   the first profile is configured to control the flow rate of respiratory gases supplied to the patient such that respiratory gases are supplied at a first substantially constant pressure for a predetermined portion of an inspiratory phase of the breathing cycle;
   the second profile is configured to control the flow rate of respiratory gases supplied to the patient such that respiratory gases are supplied at a second substantially constant pressure for a predetermined portion of an expiratory phase of the breathing cycle; and
   the first substantially constant pressure is different to the second substantially constant pressure.

4. The method of claim 1, wherein controlling the flow rate of respiratory gases comprises dynamically controlling the flow rate of respiratory gases supplied to the patient over time.

5. The method of claim 1, wherein controlling the flow rate of respiratory gases comprises varying the flow rate of respiratory gases supplied to the patient.

6. The method of claim 1, wherein controlling the flow rate of respiratory gases comprises varying the flow rate of respiratory gases supplied to the patient, wherein the varying is performed when switching between the modes and/or during one or more of the modes.

7. The method of claim 1, wherein controlling the flow rate of respiratory gases comprises varying an impedance of a gases flow path between a respiratory gases source and a patient interface or varying a flow rate of respiratory gases.

8. The method of claim 7, wherein varying the impedance of the gases flow path is achieved through use of a valve or a flow restrictor.

9. The method of claim 7, wherein varying the flow rate of respiratory gases is achieved by controlling the speed of a motor of a gases flow generator.

10. The method of claim 1, wherein pressure is determined by calculation from at least one of: pressure measured by a pressure sensor, a flow rate measured by a flow sensor, a motor speed, and a known pressure drop across the gases flow path/circuit.

11. A respiratory assistance device comprising:
    a flow generator for delivering a respiratory gases to a patient;
    a non-sealing interface in fluid communication with the flow generator and providing the respiratory gases to the patient;
    a controller configured to control a flow rate of respiratory gases supplied to a patient according to a predetermined gases flow rate profile in a mode defined for at least a portion of a breathing cycle of the patient,
    wherein the predetermined gases flow rate profile is configured to control the flow rate of respiratory gases supplied to the patient such that respiratory gases are supplied at a substantially constant pressure over the entire expiratory phase of the breathing cycle wherein the flow rate is variable.

12. The respiratory assistance device of claim 11, wherein the controller is configured to control the flow rate of respiratory gases supplied to the patient according to a first predetermined gases pressure/flow rate profile in a first mode, wherein the controller is configured to control the flow rate of respiratory gases supplied to the patient according to a second predetermined gases pressure/flow rate profile in a second mode, wherein the second predetermined gases pressure/flow rate profile is different to the first predetermined gases pressure/flow rate profile.

13. The respiratory assistance device of claim 12, wherein the first profile is configured to control the flow rate of respiratory gases supplied to the patient such that respiratory gases are supplied at a first substantially constant pressure for a predetermined portion of an inspiratory phase of the breathing cycle, wherein the second profile is configured to control the flow rate of respiratory gases supplied to the patient such that respiratory gases are supplied at a second substantially constant pressure for a predetermined portion of an expiratory phase of the breathing cycle, wherein the first substantially constant pressure is different to the second substantially constant pressure.

14. The respiratory assistance device of claim 11, wherein the controller is configured to dynamically control the flow rate of respiratory gases supplied to the patient over time.

15. The respiratory assistance device of claim 11, wherein the controller is configured to vary the flow rate of respiratory gases supplied to the patient.

16. The respiratory assistance device of claim 11, wherein the controller is configured to vary the flow rate of respiratory gases supplied to the patient, wherein the varying is performed when switching between the modes and/or during one or more of the modes.

17. The respiratory assistance device of claim 11, wherein the controller is configured to vary an impedance of a gases flow path between a respiratory gases source and a patient interface or wherein the controller is configured to vary a flow rate of respiratory gases.

18. The respiratory assistance device of claim 17, wherein varying the impedance of the gases flow path is achieved through use of a valve or a flow restrictor.

19. The respiratory assistance device of claim 17, wherein varying the flow rate of respiratory gases is achieved by controlling the speed of a motor of a gases flow generator.

20. The respiratory assistance device of claim 11, wherein pressure is determined by calculation from at least one of: pressure measured by a pressure sensor, a flow rate measured by a flow sensor, a motor speed, and a known pressure drop across the gases flow path/circuit.

21. The method of claim 1, wherein the respiratory gases are supplied to the patient using a high flow respiratory system comprising a flow generator for delivering a high flow of respiratory gases to the patient and the nasal cannula is in fluid communication with the flow generator.

22. The method of claim 21, wherein the flow rate of respiratory gases supplied to the patient is between 10 L/min and 80 L/min.

* * * * *